(12) United States Patent
Verkaart et al.

(10) Patent No.: US 6,663,586 B2
(45) Date of Patent: Dec. 16, 2003

(54) SYSTEM FOR COLLECTION OF BLOOD WITHOUT DAMAGE

(75) Inventors: Wesley H. Verkaart, Norwell, MA (US); James R. Ellsworth, Norwell, MA (US)

(73) Assignee: Harvest Technologies Corporation, Plymouth, MA (US)

( * ) Notice: Subject to any disclaimer, the term of this patent is extended or adjusted under 35 U.S.C. 154(b) by 0 days.

(21) Appl. No.: 10/040,427

(22) Filed: Jan. 9, 2002

(65) Prior Publication Data

US 2002/0055725 A1 May 9, 2002

Related U.S. Application Data

(62) Division of application No. 09/051,480, filed on Jun. 17, 1998, now Pat. No. 6,342,048.
(60) Provisional application No. 60/008,127, filed on Oct. 20, 1995, provisional application No. 60/008,128, filed on Oct. 20, 1995, provisional application No. 60/005,772, filed on Oct. 20, 1995, provisional application No. 60/020,754, filed on Jun. 28, 1996, and provisional application No. 60/020,752, filed on Jun. 28, 1996.

(30) Foreign Application Priority Data

Oct. 18, 1996 (WO) .............................. PCT/US96/16771

(51) Int. Cl.[7] .............................................. A61M 31/00
(52) U.S. Cl. .............................. 604/65; 604/4; 604/119; 604/323; 604/902; 600/378; 600/379; 417/38
(58) Field of Search .......................... 604/65, 66, 118, 604/119, 319, 323, 320, 902; 600/573, 577, 578, 579; 138/45; 417/38

(56) References Cited

U.S. PATENT DOCUMENTS

| 3,191,600 | A | * | 6/1965 | Everett | 128/276 |
|---|---|---|---|---|---|
| 3,623,483 | A | * | 11/1971 | Dyer, Jr. | 128/276 |
| 3,799,702 | A | * | 3/1974 | Weishaar | 417/38 |
| 4,135,647 | A | | 1/1979 | Mascia et al. | |
| 4,191,204 | A | * | 3/1980 | Nehring | 137/205 |
| 4,266,559 | A | | 5/1981 | Akhavi | |
| 4,275,731 | A | | 6/1981 | Nichols | |
| 4,416,658 | A | * | 11/1983 | Numazawa et al. | 604/48 |
| 4,642,093 | A | | 2/1987 | Harle | |
| 4,650,477 | A | | 3/1987 | Johnson | 604/321 |
| 4,681,571 | A | | 7/1987 | Nehring | |
| 4,735,606 | A | | 4/1988 | Davision | 604/118 |
| 4,799,925 | A | | 1/1989 | Rosenblatt | 604/181 |
| 4,923,451 | A | | 5/1990 | McCormick | 604/321 |
| 5,000,351 | A | | 3/1991 | Rudick | |
| 5,002,534 | A | | 3/1991 | Rosenblatt | |
| 5,024,615 | A | | 6/1991 | Buchel | 604/119 |
| 5,141,504 | A | * | 8/1992 | Herweck et al. | 604/317 |
| 5,411,472 | A | * | 5/1995 | Steg, Jr. et al. | 604/4 |
| 5,656,027 | A | * | 8/1997 | Ellingboe | 604/49 |
| 5,971,956 | A | * | 10/1999 | Epstein | 604/119 |
| 5,984,892 | A | * | 11/1999 | Bedingham | 604/67 |
| 6,024,731 | A | * | 2/2000 | Seddon et al. | 604/317 |
| 6,517,512 | B1 | * | 2/2003 | Bock et al. | 604/67 |
| 6,547,775 | B1 | * | 4/2003 | Blyakman | 604/505 |

FOREIGN PATENT DOCUMENTS

EP 0 092 313 A2 * 10/1983 ............ A61M/1/02
EP 0254607 1/1988

* cited by examiner

Primary Examiner—Weilun Lo
Assistant Examiner—Michael Bogart
(74) Attorney, Agent, or Firm—Clark & Brody

(57) ABSTRACT

A system for the collection of physiological fluids includes a vacuum source (14) that is controlled to provide low vacuum as a function of whether fluids are entering the system. The suction wand and associated tubing are made of thin flexible materials, and the pressures employed do little damage to the collected fluids.

5 Claims, 4 Drawing Sheets

SYSTEM FOR COLLECTION OF BLOOD WITHOUT DAMAGE

"This application is a division of application Ser. No. 09/051,480 filed Jun. 17, 1998, now U.S. Pat. No. 6,342,048, which claims benefit of application Serial No. 60/008,127 filed Oct. 20, 1995, and claims benefit of application Serial No. 60/008,128 filed Oct. 20, 1995, and claims benefit of application Serial No. 60/005,772 filed Oct. 20, 1995, and claims benefit of application Serial No. 60/020,754 filed Jun. 28, 1996, and claims benefit of application Serial No. 60/020,752 filed Jun. 28, 1996."

TECHNICAL FIELD

This invention relates to the art of systems for recovery of physiological fluids, such as blood. In the preferred embodiment, the invention relates to a system for collection of blood during surgery and for returning the collected blood to the patient.

BACKGROUND

Systems for collection of blood during surgery for the purpose of returning the blood to the patient are known. These systems typically are vacuum systems that rely on sources of low pressure existing in the hospitals to create the suction required for collecting the blood. The collected blood may be washed by any of several known cell washing devices prior to providing the collected blood back to the patient.

Because blood cells are very fragile, they are frequently damaged during the collection process, which makes them unavailable for return to the patient. For example, cells will be damaged if subjected to excessive physical contact, such as turbulence or compression. For example, collection systems that use roller pumps cause excessive physical damage. Similarly cells subjected to pressure differentials that are too great will be damaged. Thus, blood cells subjected during vacuuming operations to exterior pressures that are too low will burst and not be available for return to the patient.

Although the use of vacuum is well known in the art, conventional systems use high vacuum (in excess of 250 mmHg), which is throttled by simple mechanical regulators. These systems do not employ a "feed-back loop" or other sensing circuits to monitor vacuum parameters. Such systems are not optimal for collecting shed blood and are known to cause significant damage to collected red cells.

Mechanically regulating vacuum to −100–150 mmHg (dead end) can reduce the red cell damage greatly, but significant red cell damage occurs nevertheless and the problem is compounded by lack of understanding by the user of correct adjustment technique.

Systems that rely on the source of vacuum pressure typically used in hospitals frequently subject the cells to very low pressures, which severely damages the cells. Standard surgical suckers have an opening at the tip of about 0.125 to 0.150 inch, and the standard surgical suction tubing is usually 0.25 inch, (inside diameter), but may be as large as 0.281 inch (inside diameter). The connections between these components or to a standard collection chamber may incorporate substantial changes in diameter and possibly have reduced diameters at the connection points. The vacuum levels for suction collection of shed blood for return to a patient are recommended in the prior art (Autotransfusion Standards, American Association of Blood Banks) to be in the range of from −100 mmHg to −150 mmHg. This standard assumes the use of the above standard sucker and suction tubing.

Thus, there is a need for methods and apparatus that rapidly collect shed blood in surgery and trauma and do not damage the blood during collection. A need also exists for systems that safely collect shed blood that has formed into small, shallow pools in the surgical site, a process known as "skimming." A further need exists for a suction (vacuum) system that does not exert large pressures on tissues in the surgical area while the blood is collected. Such systems are known as atraumatic systems.

Although portable suction devices for various application are known in the art, there has never been a blood collection system with all parameters optimized which can collect blood at high flow rates, allow skimming, and not subject cells and tissues to trauma.

SUMMARY OF THE INVENTION

In accordance with the invention a portable, electrically-powered blood collection system collects blood substantially without damage to the blood cells. The collected fluids are filtered and placed in a flexible bag to facilitate their return to the patient. The system is self-contained and requires only external electric power in one version and no external power in a second version. Minimal damage to the collected blood is obtained by optimization of the physical characteristics of the system. Further, the system conditions the collected blood and maintains it in a safe condition until a volume has been collected that is sufficient to warrant returning the blood to the patient. The system immediately and effectively packages the collected blood for convenient return to the patient by conventional IV administration techniques.

The blood collection system of the invention uses an electronically-controlled pump to create a low pressure flow of air to aspirate shed blood. An electronic circuit increases and decreases the vacuum parameters, such as pressure and flow rate, according to need, by sensing no load, low load and high load situations. Under a no load condition, e.g., air flow only, and a low load condition, e.g., surface suctioning air mixed with mostly foam, the system maintains a very low vacuum of about 20 mmHg and a correspondingly small rate of air flow. Under high load conditions, e.g., where the tip of the aspiration tool is immersed in a pool of blood or is occluded, the system instantaneously increases the vacuum to about −100 mmHg. Because the flow in the high load condition is almost all liquid, the flow velocity through the aspiration path is low (Poiselle-Hagen Law). In this system, the blood being collected is never exposed to the high vacuum or velocity that would damage the cells, and laboratory testing using these control parameters has shown insignificant levels of blood damage.

The collection/suction tube of the invention preferably has a thin wall, whereby it is lightweight and easy to use. Because the vacuum level is controlled and small, however, there is little danger that the tube wall will collapse when the tip is occluded.

The system of the invention preferably includes a large-bore sucker, the opening at the tip having a diameter of between 0.285 and 0.500 inch. The bore of the sucker continues unreduced to its connection with the suction tubing, which has a nearly equal diameter, and the two components are connected by a coupler that provides an unrestricted, smooth transition between them. The large bore sucker and tubing are connected to a collection chamber equipped with an equally large bore fitting. A suitable coupler is employed to allow an unrestricted and smooth transition between the tubing and chamber fitting.

The sucker assembly described above is connected to a vacuum source capable of regulating the vacuum at very low levels. The preferred embodiment of the system regulates the vacuum between −10 mmHg and −100 mmHg. The particular level of the vacuum is based on the demand and is governed by feedback through the sucker, tubing and collection chamber to the vacuum source. The pressure differential across a mechanical resistor in the vacuum line is sensed by pressure transducers and resulting signals are fed to a suitable electronic regulating source, which, in turn, operates the vacuum source in a pulsed mode, alternating between on and off conditions as required to maintain the desired vacuum for the particular demand condition.

With an open suction line (carrying no liquid) the resistance across the mechanical resistor is minimal and the vacuum is reduced to the minimum level. During skimming, there is increased resistance through the tubing and across the mechanical resistor, so the vacuum is slightly increased. With the collection of some pooled liquid there will be further resistance, so the vacuum level will further increase proportionately. With full immersion of the sucker tip in liquid, the vacuum resistance through the system will be at a maximum level, and the vacuum will then be controlled to be the largest level of −100 mmHg.

A general observation of fluid mechanics is that the rate of fluid flow through a tube is a function of the $4^{th}$ power of the radius of the tube. Thus, a slight increase in the internal diameter of a tube results in a significant increase in the flow rate, all other conditions being equal. Recognizing this relationship, the system of the invention utilizes larger bore tubing to permit lower operating vacuum levels, which minimizes damage to the collected blood and avoids tissue trauma. Increasing the tubing diameter in accordance with the invention more than compensates for the reduction in vacuum levels by providing a larger than expected flow rate for these vacuum levels. The low vacuum levels used by the system of the invention could not provide flow rates acceptable to surgeons with standard bore suckers. Thus, the combination of the large bore sucker, tubing and connectors with lower vacuum levels is important.

Because the tubing has a larger bore, fluid moves through the tube more slowly while still achieving the desired flow rate. This is advantageous because less damage is caused to slowly moving blood than to faster moving blood. Another advantage is that the less-restricted pathway of the large bore system significantly reduces the potential for clogging the tube with debris during the surgical procedure. There are two reasons for this. First, the increased diameter has the ability to pass more potentially-clogging particles and, second, the unrestricted path allows potentially clogging solids to pass all the way through to the collection chamber.

The low pressures of the system (i.e., the maximum of −100 mmHg) also reduces or eliminates trauma to tissues and also reduces the tendency of the suction to "grab" the tissue, known as invagination.

Yet another advantage of the small negative pressures employed in the invention is that the tubing may be made of thinner, more flexible materials. Prior art suction tubing must be able to withstand up to −600 mmHg because it may encounter vacuum levels this high when connected to standard hospital suction systems. Standard suction tubing has an internal diameter (ID) of 0.250 inch and an outside diameter (OD) of 0.375 inch and is made of PVC having a Durometer value high enough to prevent collapse at the maximum vacuum. The tubing of the invention may use lighter, thinner walled tubing because the vacuum is controlled to have a maximum of −100 mmHg. In the preferred embodiment, the tubing has an ID of 0.300 inch and an OD of 0.380 inch. The thinner wall also makes the tubing more flexible; a highly desirable feature in surgery.

Another feature of the invention is its manner of treating the collected blood with anti-coagulant, a significant aspect of conditioning all collected blood. Anti-coagulation has conventionally been achieved by the addition of a solution containing chemicals (typically heparin or citrate) which inhibit the normal clotting reaction of the blood to air and foreign substances. The proper ratio must be achieved; enough must be added to prevent clotting while too much anti-coagulant makes it difficult or impossible for the body to metabolize and may cause negative side effects, such as cardiac instability.

In accordance with the invention, the anti-coagulant is pulled into the collection chamber by the vacuum in the collection chamber. The amount of anti-coagulant varies with the vacuum level. Thus, the invention uses the controlled vacuum feature to regulate anti-coagulant flow in proportion to the volume of blood being collected. Under no load or low load conditions, the flow rate of the anti-coagulant is very low (a drip). Under high load, the vacuum in the system increases and draws significantly more anti-coagulant into the collection chamber (a stream). A disc of porous plastic is employed as a type of "orifice plate" to amplify the effect of the pressure differentials between no/low/high demand conditions. Alternately, an elastomer disc with one or more slits through it may be used for the same purpose.

Since both air and blood are pulled into the system by vacuum, the air must be continuously separated from the blood and exhausted. The collected blood and anticoagulant are introduced tangentially into a largely cylindrical collection chamber where the air is separated and exhausted out the top of the collection chamber. The blood/anti-coagulant mixture is filtered and accumulates in the bottom of the collection chamber.

Once sufficient volume has been collected for re-infusion, the blood/anti-coagulant mixture is pumped, preferably by a roller pump, to a re-infusion bag with an integral filter. "Sufficient volume" depends on the patient and nature of the case and is typically about 200–600 ml. The design and speed of the roller pump/pump tube combination is such that blood damage is very small. Also, the roller pump is operated independently of the vacuum, which allows the bags to be filled while the vacuum is simultaneously operated.

The mixture of collected blood and anti-coagulant is pumped into a re-infusion bag with a built in 40 micron filter. The blood is pumped to the bag through a tube from the collection chamber. The tube is attached to the chamber through Luer locks, which are known in the art, to provide easy disconnection of the bag. After the filter bag inlet is clamped and disconnected, it is hung on an IV pole and the contents re-infused using conventional IV administration techniques. All of the blood/anti-coagulant mixture administered to the patient in this way passes through the 40 micron filter.

All vacuum blood collection systems require some method of preventing overflow of blood into the vacuum source in the event of a full collection chamber. The invention uses two systems; an electronic primary and mechanical back-up.

The level of blood/anti-coagulant mixture is sensed opto-electronically. Capacitance, ultrasound or other level sensing means well known in the art could be used alternately. The electronic circuit terminates operation of the vacuum pump at a predetermined level of blood, thus generally preventing overflow of the liquid into the vacuum system. Additional levels may be sensed to provide useful signals, such as nearly full, or nearly empty, etc., which may be employed to activate the roller pump to discharge the collection chamber or to warn an operator by auditory or visual signals.

A mechanical back-up feature is provided to prevent damage to the electric vacuum pump and other parts of the hardware in the event of failure of the electronic level sensing. A fluid stop, which is preferably a cylinder of porous plastic having a self sealing feature, such as application of self sealing Porex, is interposed between the collection chamber vacuum port and the air tube leading to the electric vacuum pump inlet. Fluid entering the fluid stop will activate the self sealing property of the material to effectively prevent flow of air or liquid, thus preventing further overflow. Once the level in the collection chamber is reduced, a new fluid stop must be installed to return the system to normal operation.

As collected fluid is pumped into bags, the weight or volume pumped is accumulated by an electronic circuit. A display indicates the weight or volume of a first bag when it is removed. Then, when the second bag is filled and removed, the display shows the weight or volume of both bags, and so on. Thus, the operator may easily determine the total amount of blood pumped to the bags for re-infusion.

Because the air flowing through the device was initially mixed with blood, it must be considered a biological hazard. The hardware unit of the invention is equipped with an easily changed exhaust filter that removes any airborne particulates. The user simply changes this filter periodically.

DETAILED DESCRIPTION OF THE PREFERRED EMBODIMENT

Figure 1:
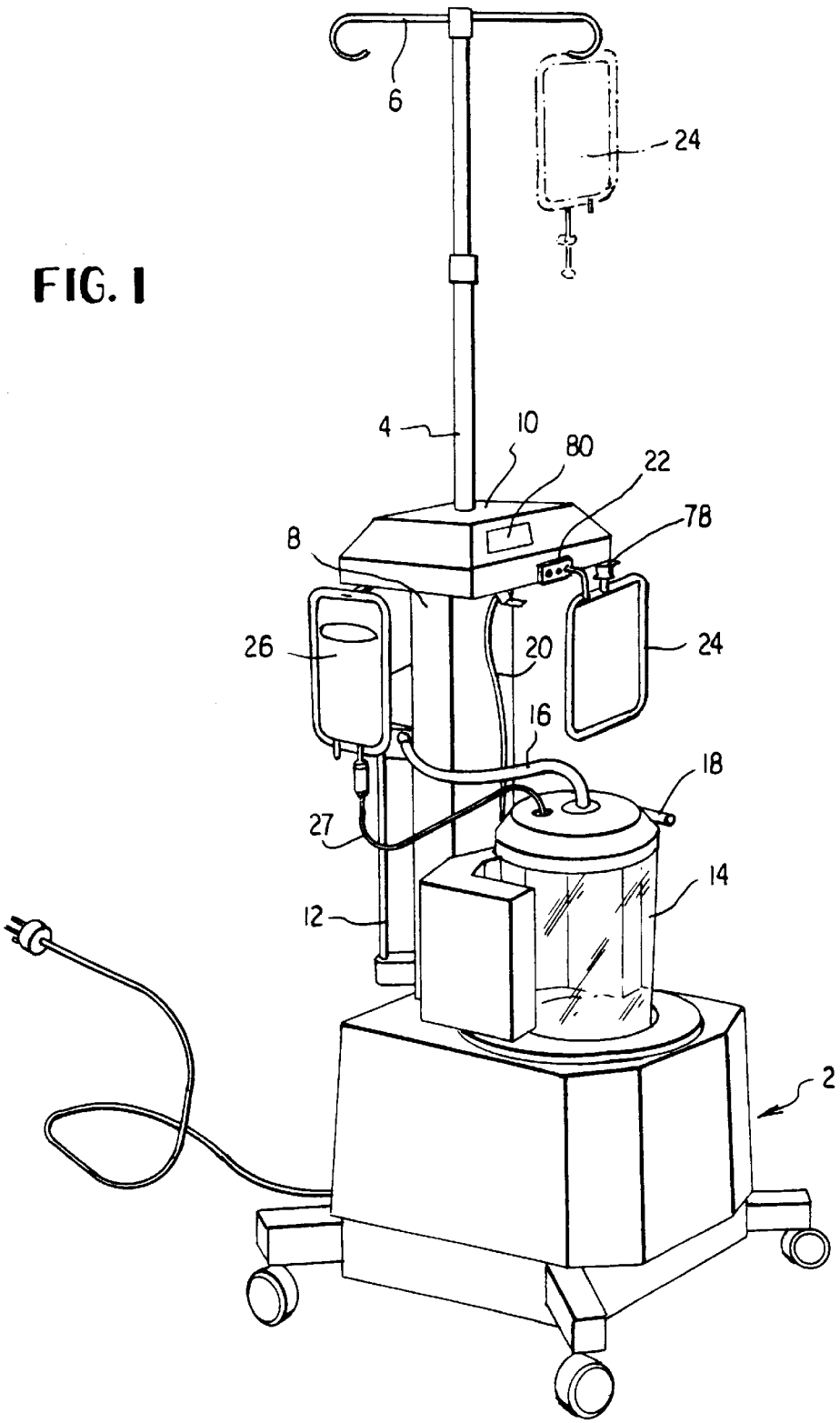
FIG. 1 is a perspective of a blood collection system according to the invention.

With reference to FIG. 1, a blood collection system according to the invention comprises a wheeled base unit 2, which supports the main components of the system and provides a convenient means for transporting the system to a surgical site. A vertical post 4 extends upward from the base and includes a cross piece 6 similar to the known IV pole. A support pillar 8 extends upward from the wheeled base and is preferably coaxial with pole 4, and a horizontal platform 10 is located at the top of the pillar.

A vacuum source (see FIG. 2) is located within the base 2, and that source is connected to the central part of an overflow protector 12, which will be described in detail in connection with FIG. 3. The outer part of the overflow protector 12 is connected to a collection chamber, or reservoir, 14 by tubing 16. The vacuum applied through tubing 16 reduces the pressure in the collection chamber 14 whereby fluids will be drawn into the chamber through inlet 18. Inlet 18 is located on the side of an upper, cylindrical part of the chamber whereby the fluids flowing into the chamber will flow generally in a direction tangential to the cylinder. Centrifugal forces arising from this flow will tend to throw the fluids outward, thus separating the fluids from the air.

An outlet tube 20 from the collection chamber extends from the bottom of the chamber upward to a connector element 22, which allows removable connection with a collection bag 24. A pump, preferably a roller pump, located in the base pumps the fluids which have collected in the chamber upward and into the bag 24.

Preferably the bag 24 includes a filter for removing particles larger than about 40 microns.

Anti-coagulant is supplied by a bag 26. A tube 27 extends from the bag 26 to a second inlet of the chamber 14 whereby anti-coagulant will be drawn into the chamber along with the collected blood by the vacuum in the chamber. The level of vacuum in the chamber is based on the demand for suction, as will be described with respect to FIG. 4. Thus, the vacuum level is higher when the system in suctioning fluids than when only air is flowing in the suction tube. Because the amount of anti-coagulant that is drawn into the chamber is a function of the vacuum, it follows that the amount of anti-coagulant drawn into the chamber correlates with the amount of fluid drawn in. This maintains a constant ratio between the fluid and the anti-coagulant for varying fluid flow rates.

Figure 2:
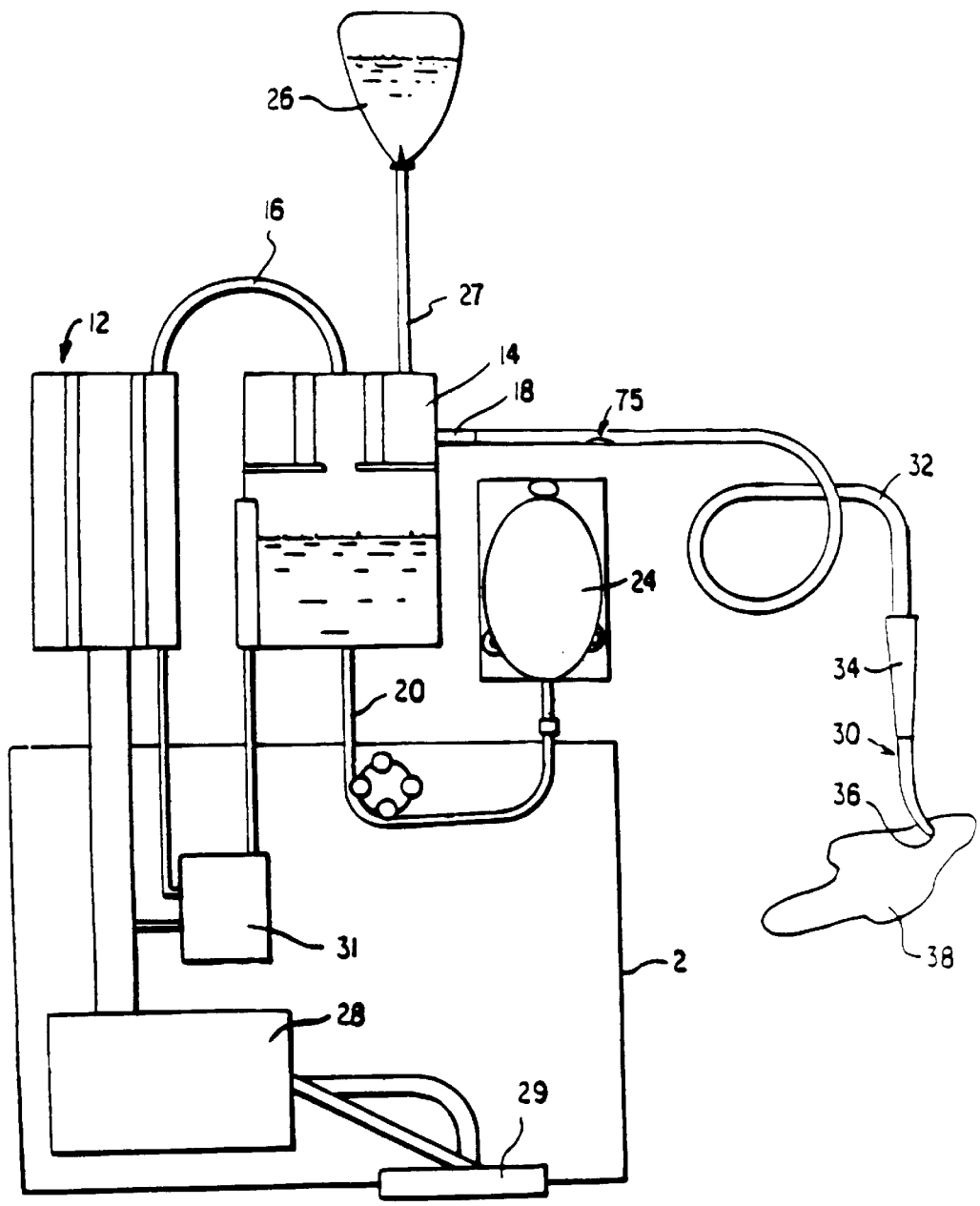
FIG. 2 is a schematic diagram of the major components of the system shown in FIG. 1.

Referring now to FIG. 2, the major components of the system are shown schematically. An electric vacuum pump 28, preferably a pump driven by a linear piston motor, is connected to the central portion of the overflow protector 12 and the collection chamber 14. The inlet 18 to the collection chamber is connected to a wand, or sucker, 30 by way of tubing 32. The wand is generally tubular and provides a hand grip portion 34 and an inlet opening 36 for easily collecting blood from a pool 38 of blood or directly from a patient (not shown). In accordance with the invention, the diameter of the wand inlet opening 36 is larger than in the prior art and preferably in the range of from 0.285 inch to 0.500 inch. Similarly, in the preferred embodiment, the tubing 32 has an ID of about 0.300 inch and an OD of about 0.380 inch.

An exhaust filter 29 is connected to the outlet of the vacuum pump. This filter is easily replaced and includes sound reduction features to reduce the noise from the pump. The electronics package is shown at 31 and includes the control logic circuits described in connection with FIG. 4 as well and other well-known electronic components.

Figures 3A, 3B:
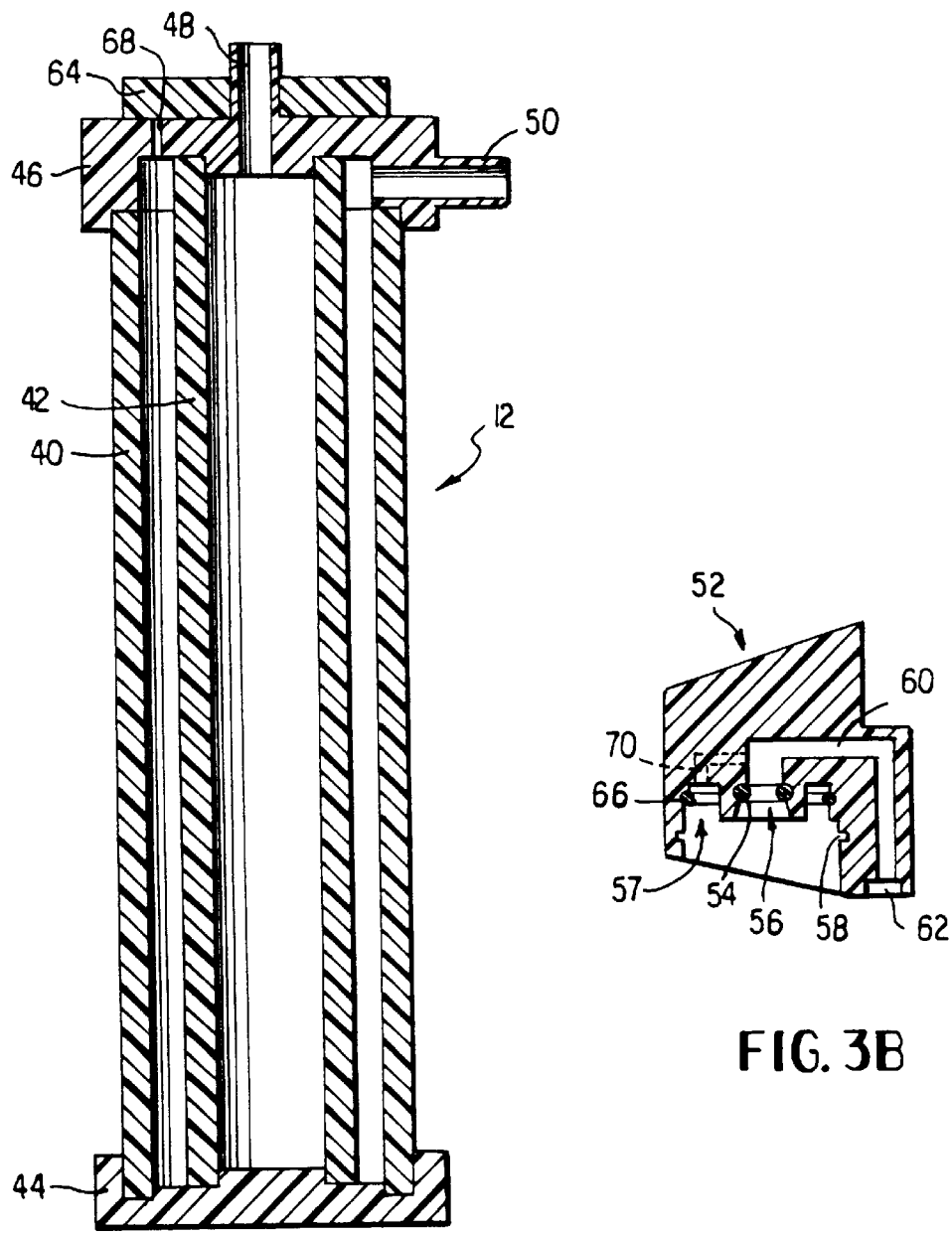
FIG. 3A is a vertical cross section of an overflow prevention component according to one aspect of the invention.
FIG. 3B is a vertical cross section of a vacuum socket.

The overflow prevention element 12 of the invention is shown in vertical cross section in FIG. 3A. Element 12 comprises an outer cylinder 40, preferably of transparent plastic, and an inner cylinder 42. The inner cylinder is made of a porous plastic material that is self-sealing. Such a material is sold under the name Porex Self Sealing and may be obtained from the Porex Corporation. The two cylinders are engaged at one end by a cap 44, which closes the lower end of each cylinder. A machined end cap 46 is attached to the opposite ends of the cylinders. The end cap 46 includes annular recesses, which receive the respective ends of the two cylinders and provide a primary vacuum port 48, which communicates with the interior of the inner cylinder 42, and an inlet port 50, which communicates with the annular space between the two cylinders. The vacuum source 28 is connected to the primary vacuum port, and the blood collection chamber 14 is connected to the inlet port via tube 16.

Figure 4:
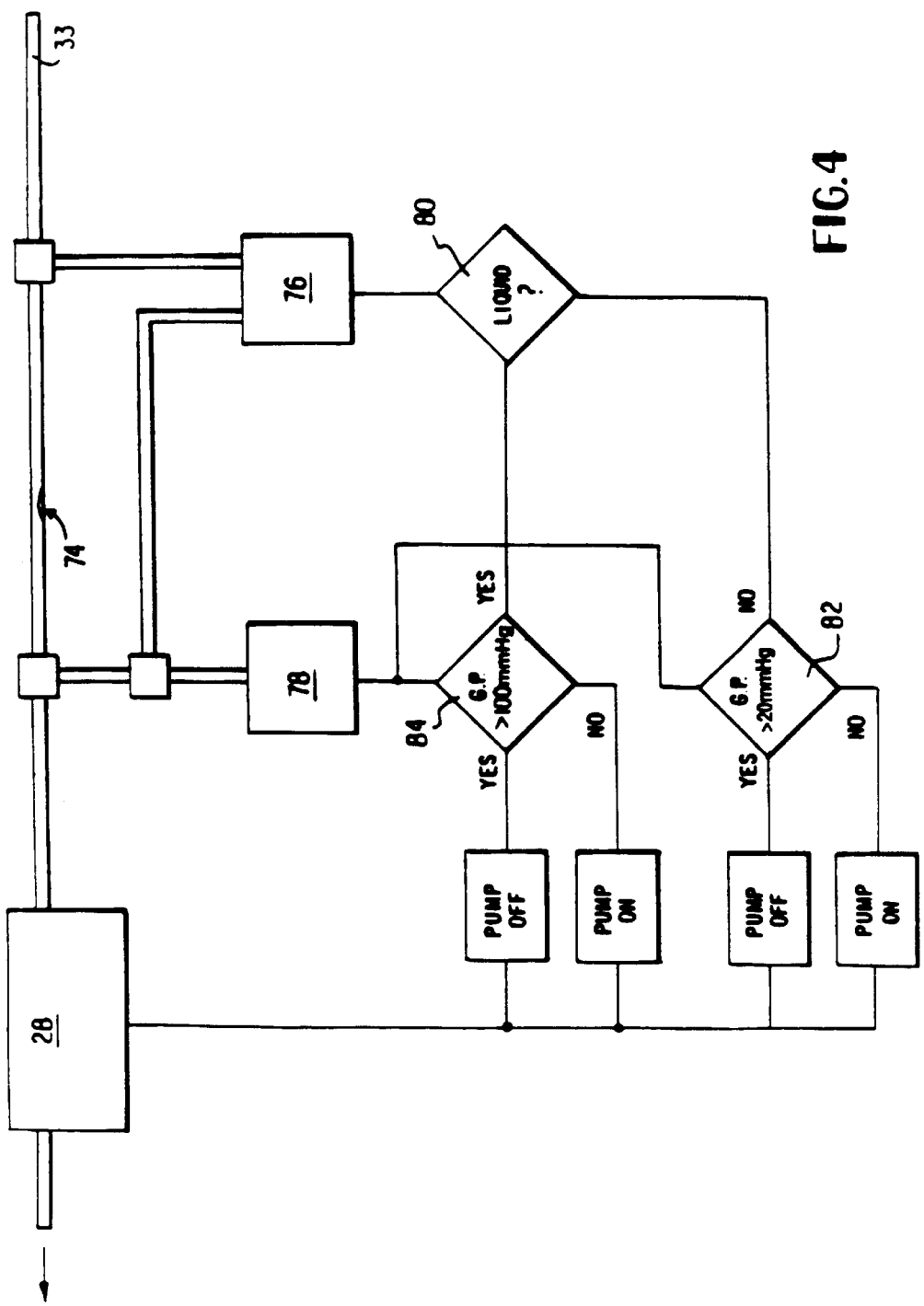
FIG. 4 is a schematic diagram of the vacuum control circuit according to one aspect of the invention.

The overflow protection device 12 is connected to the pillar 8 by a vacuum socket 52 shown in FIG. 3B in vertical cross section. The port 48 is received in an O-ring 54 in recess 56 in the vacuum socket. The recess communicates with a channel 60, which terminates in a nipple 62 connected to the vacuum pump 28 via an inlet tube 33 (FIG. 4).

Device 12 also includes a collar 64, which forms an annular space with the port 48. The outer surface of the collar 64 is received in an O-ring 66 in a recess 57 in the socket 52. The collar communicates with the annular space between the outer and inner cylinders via pressure sensing port 68. This pressure is transmitted via channel 70 in the vacuum socket when the device 12 is installed.

The vacuum socket is attached to the pillar 8 at projection a projection. The device 12 is, in turn, attached to the socket by a bayonet mount 58, which engages ears (not shown) on the machined cap 46. The device 12 is a disposable element, and attachment is made by urging the machined cap 46 into the vacuum socket 52 and twisting to fix the bayonet connection.

The operation of the device 12 is as follows. During normal operation, air is drawn through the port 48, the self-sealing cylinder 42, the port 50, the collection chamber 14, and the wand 30. Fluid carried by the airflow is removed from the air in the chamber and falls to the bottom of the chamber. In the event, however, that the collection chamber becomes full and fluid overflows into the port 50, the blood entering the device will wet the porous plastic cylinder. This will clog the cylinder 42 and seal off the flow of liquid through the cylinder. If only a small amount of fluid makes it to the cylinder 42, the air will continue flowing but the fluid will be trapped by the cylinder. If a large amount of fluid makes it to the space between the cylinders, the cylinder 42 will clog completely, and all fluid flow will stop. The device 42 would then require replacement. Because the cylinder 40 is transparent the overflow situation is obvious to the operator.

Then second O-ring seal provides an air pathway for sensing pressure in the space between the outside of the porous plastic material of the inner cylinder and the inner wall of the outer cylinder. This sensing is useful for monitoring the condition of the device 12, e.g., whether it is clogged, and in certain vacuum control applications. The determination of clogging is preferably part of an interlock system that shuts off the vacuum source when it detects clogging. Similarly, pressure in the port 68 that is too low indicates improper connection of the device and prevents operation of the vacuum source. Overflow may also be sensed optically by directing a beam of light into the outer cylinder and measuring the refraction. If the outer cylinder is filled with fluid, the refraction will be less than if empty, and this may be detected with a photo sensor. The O-rings may be components of the overflow prevention device or components of the socket into which it mounts. Other types of fittings may be used as known in the art.

The device 12 may be secured in its socket by friction, fasteners a cam (bayonet) mount, or other mechanical means. It should be mounted vertically for best performance and proper use of the pressure sensing port.

Because the porous plastic presents resistance to flow of air, it must have sufficient surface area for the specific application. Simply changing the length of the preferred embodiment easily and inexpensively accomplishes this adjustment. A cylindrical tube-in-tube design is shown for the preferred embodiment as it is easy to manufacture. Other shapes and multiple inner porous elements within a housing are possible variations.

The control system of the invention will be described with respect to FIG. 4. During vacuum clearing of fluids from a surgical field of fluids, the fluid is taken into the vacuum line by immersion of a sucker tip into a pool of blood or by moving the sucker tip over the surface by an operation referred to as skimming. Skimming with high levels of vacuum (i.e., less than −100 mmHg) causes hemolysis of the blood, precluding its re-infusion into the patient. According to the invention the vacuum is held at a lower level when the skimming is in process so that the yield of infusible materials increases. When the system senses that the fluid is being taken up from a pool, the system increases the vacuum to a higher level, but nonetheless a safe level for pool evacuation. The higher level facilitates a maximum rate of evacuation of the operating field and maintains a high yield of infusible materials.

In the system of the invention, the vacuum source 28 is a pump driven by a linear piston motor. The input to the vacuum source is an open ended pathway, i.e., the tube, 32, of some length and of various shapes and including various components. The tube causes pressure drops along its length that approximately add up to the vacuum level at the vacuum source. The pressures are relative to atmospheric pressure and the pressure at the open end of the tube is atmospheric. A pressure restriction 74 is placed in the line, and a pressure transducer 76 is connected to locations in the tube on opposite sides of the restriction 74 to sense the difference in pressure across the restriction. As air flow through the tube increases, the pressure drop across the restriction increases. Air flow will increase due to either an increase in the vacuum level or a reduction in other restrictions in the system, such as fluids 75 being pulled into the tube. An increase in restriction is caused by the introduction of fluid into the tube.

The pressure transducer 76 is preferably a piezoelectric sensor in a bridge circuit, whereby a signal is generated in response to changes in the differential pressure across restriction 74.

A second pressure transducer 78, similar physically to transducer 76, is connected to the tube near the vacuum source to detect the gauge pressure of the vacuum source.

A first logic circuit 80 detects the signals from the transducer 76 to determine whether air alone or a mixture of air and liquid are flowing in the tube 32. As noted, this determination is made as a function of the pressure drop across the restriction 74. If only air is flowing in the tube 32, the electric pressure source is driven to produce a low vacuum, such as −20 mmHg. This is accomplished, for example, by the logic circuit 82, which also receives input from the gauge pressure transducer 78. If the gauge pressure is less than −20 mmHg, the pump is turned off, and if the pressure is greater than −20 mmHg, the pump is activated. Thus, the pump is pulsed to maintain the desired −20 mmHg pressure. Similarly, if the circuit 80 determines that liquid is being pulled into the system, the pump is controlled to increase the vacuum to about −100 mmHg. This is accomplished by logic circuit 84, which is also connected to the gauge pressure transducer 78 to pulse the motor of the vacuum source 28 to produce a desired pressure of about −100 mmHg.

Referring again to FIG. 1, the system of the invention includes a support 78 for the bag 24 being filled. This support may be attached to a weighing device whereby the weight or volume of the fluid pumped into the bag is measured. This weight or volume is displayed on the display 80. Preferably, the weight or volume is accumulated for all of the bags for a particular procedure. Thus, the display will show the accumulated weight or volume of fluids recovered from the patient.

FIG. 1 also shows a bag 24 in phantom lines supported from the cross piece 6. This is the position the bag would be in during re-infusion. It will be appreciated that the bag is turned over compared to its position when filling.

The electronics may be a conventional hard wired system with individual components or it may be an appropriately programmed microprocessor.

The vacuum is preferably provided by a linear piston type motor. Such may be obtained from MEDO Corporation of Hanover Park Ill.

We claim:

1. In a system for collecting physiological fluids of the type having a suction wand operatively connected to a source of reduced pressure by a tube, the method comprising the steps of:

applying said reduced pressure to said tube, detecting when said fluids are present in said suction tube;

maintaining said source of reduced pressure at a first pressure when said fluids are not present in said suction wand in such a manner that air is drawn into said suction wand at a first rate; and maintaining said source of reduced pressure at a second pressure when said fluids are present in said suction wand in such a manner that said fluids are drawn into said suction wand at a flow rate that is less than said first rate.

2. A system according to claim 1 wherein said first pressure is in the range of from about −20 mm Hg to about −10 mm Hg and said second pressure is in the range of from about −150 mm Hg to about −100 mm Hg.

3. A system according to claim 1 wherein said step of detecting comprises measuring the pressure difference across a flow restriction in a flow channel connected between said suction wand and said source of reduced pressure.

4. A system according to claim 1 further comprising the step of skimming said physiological fluids when said source of reduced pressure is maintained at said first pressure.

5. In a system for collecting physiological fluids of the type having a suction wand operatively connected to a source of reduced pressure, the method comprising the steps of:

detecting when said fluids are present in said suction wand;

maintaining said source of reduced pressure at a first pressure when said fluids are not present in said suction wand; and maintaining said source of reduced pressure at a second pressure when said fluids are present in said suction wand, wherein said first pressure is in the range of from about −20 mm Hg to about −10 mm Hg and said second pressure is in the range of from about −150 mm Hg to about −100 mm Hg.

* * * * *